United States Patent [19]
Wochnowski

[11] Patent Number: 4,967,739
[45] Date of Patent: Nov. 6, 1990

[54] METHOD OF AND APPARATUS FOR MAKING ROD-SHAPED ARTICLES OF THE TOBACCO PROCESSING INDUSTRY

[75] Inventor: Waldemar Wochnowski, Hamburg, Fed. Rep. of Germany

[73] Assignee: Körber AG, Hamburg, Fed. Rep. of Germany

[21] Appl. No.: 364,302

[22] Filed: Jun. 9, 1989

[30] Foreign Application Priority Data

Jun. 11, 1988 [DE] Fed. Rep. of Germany ....... 3820015
Sep. 21, 1988 [DE] Fed. Rep. of Germany ....... 3832008

[51] Int. Cl.$^5$ .............................................. A24C 5/18
[52] U.S. Cl. .................................. 131/84.1; 131/84.4; 131/906
[58] Field of Search ..................... 131/84.1, 84.2, 84.4, 131/906, 905, 908, 910

[56] References Cited

U.S. PATENT DOCUMENTS 4,326,542  4/1982  Laszlo et al. ................... 131/906 X
4,522,214  6/1985  Osmalov .......................... 131/84.1
4,615,342  10/1986  Federle et al. .
4,771,794  9/1988  Gaisser et al. ..................... 131/84.1
4,836,221  6/1989  Okumoto ........................ 131/906 X

FOREIGN PATENT DOCUMENTS 2028098  3/1980  United Kingdom ............... 131/84.4
2128466  5/1984  United Kingdom ............... 131/84.4

Primary Examiner—V. Millin
Assistant Examiner—Jennifer L. Doyle
Attorney, Agent, or Firm—Peter K. Kontler

[57] ABSTRACT

Cigarettes are produced by gathering shredded tobacco into a stream which is moved longitudinally and is draped into a web of cigarette paper to form a rod which is subdivided into cigarettes of desired length. In order to impart to the cigarettes predictable characteristics, particularly hardness, draw resistance, number of puffs per cigarette, nicotine content, carbon monoxide content and tar content, the operation of the trimming device which removes the surplus from the stream prior to draping is regulated as a function of third signals which are generated on the basis of first signals denoting the monitored density of the stream, second signals denoting the monitored or calculated filling power of tobacco, and a number of functional equations which denote predetermined regular relationships between the parameters denoted by the first and second signals and the aforementioned characteristics of cigarettes.

26 Claims, 3 Drawing Sheets

METHOD OF AND APPARATUS FOR MAKING ROD-SHAPED ARTICLES OF THE TOBACCO PROCESSING INDUSTRY

BACKGROUND OF THE INVENTION

The invention relates to improvements in methods of and in apparatus for making rod-shaped articles of the tobacco processing industry, such as cigarettes, cigars, cigarillos and cheroots. More particularly, the invention relates to improvements in methods of and in apparatus for making rod-shaped articles (hereinafter called cigarettes for short) from comminuted tobacco leaves or other smokable material by converting such material (hereinafter called tobacco) into a stream which is thereupon draped into a web of wrapping material to form with the wrapping material a rod ready to be subdivided into cigarettes of desired length.

Manufacturers of cigarettes strive to produce articles of unchanging quality. Particular emphasis is placed upon certain selected characteristics of cigarettes, not only by the makers of cigarettes but also by the smokers. For example, a smoker will normally prefer cigarettes having a predetermined hardness and a particular draw resistance (namely that resistance which tobacco smoke encounters to the flow toward the mouth). On the other hand, a manufacturer of cigarettes will be particularly interested in the percentage of certain ingredients which are also of interest to authorities, such as the nicotine content, the content of condensate (tar) and, at least in certain countries, the carbon monoxide content because such information must be displayed on the packets.

It is already known to regulate the making of cigarettes in such a way that the density (and hence the weight) of cigarettes remains constant. This is achieved by monitoring the density of cigarettes and by regulating the removal of surplus tobacco from the stream in dependency upon the results of the monitoring operation. However, it is not known to select in advance certain other important characteristics of the stream and/or finished cigarettes, particularly the nicotine content, the carbon monoxide content and/or the condensate (tar) content of tobacco smoke.

OBJECTS OF THE INVENTION

An object of the invention is to provide a novel and improved method of making cigarettes which renders it possible to select in advance and to regulate the values of several important characteristics of cigarettes with a high degree of accuracy and predictability.

Another object of the invention is to provide a method which renders it possible to produce cigarettes in such a way that the value of each of a large number of important characteristics of cigarettes will remain within a selected range.

A further object of the invention is to provide a method which renders it possible to select in advance and to regulate the values of various characteristics of cigarettes during actual production in a modern high-speed cigarette making machine.

An additional object of the invention is to provide a method which can be resorted to for accurate advance determination of nicotine content, carbon monoxide content and/or condensate content of tobacco smoke.

Still another object of the invention is to provide a method which renders it possible to determine in advance certain other important characteristics of cigarettes such as the weight, the density, the hardness, the resistance to flow of tobacco smoke toward the mouth of the smoker and the number of puffs which can be made from a cigarette.

A further object of the invention is to provide a method which renders it possible to rapidly and effectively alter the value of one or more characteristics of cigarettes in the course of actual making.

Another object of the invention is to provide is to provide a method which renders it possible to optimize the values of several characteristics of cigarettes in a fully automatic way.

An additional object of the invention is to provide a novel and improved apparatus for the practice of the above outlined method.

Another object of the invention is to provide an apparatus which can be installed in existing cigarette rod making machines and can be combined with existing filter tipping and other processing machines.

A further object of the invention is to provide the apparatus with novel and improved means for controlling the conversion of a stream of comminuted tobacco and wrapping material into cigarettes in such a way that the value of a large number of important characteristics of cigarettes will match or closely approximate an optimum value.

Another object of the invention is to provide the apparatus with novel and improved combinations of means for evaluating and processing the results of monitoring of loose tobacco, a tobacco stream, a tobacco rod and/or discrete tobacco-containing articles of the tobacco processing industry.

An additional object of the invention is to provide the apparatus with novel and improved means for regulating the operation of the device which serves to remove the surplus from a stream of smokable material.

A further object of the invention is to provide the apparatus with novel and improved means for optimizing the making of cigarettes in a number of different respects which are of interest to the smoker, to the manufacturer and to the authorities.

SUMMARY OF THE INVENTION

One feature of the present invention resides in the provision of a method of making cigarettes and analogous rod-shaped articles from comminuted tobacco (e.g., from tobacco shreds) and wrapping material. The improved method comprises the steps of gathering comminuted tobacco into a continuous stream and advancing the stream longitudinally, draping the stream into a web of wrapping material, subdividing the draped stream into rod-shaped articles of selected length, monitoring a first parameter which constitutes the density of the draped or undraped stream, ascertaining a second parameter which is a parameter of tobacco or of the stream, generating first and second signals which respectively denote the first and second parameters, determining at least one selected characteristic (such as the desired nicotine content, the desired carbon monoxide content of tobacco smoke or the desired condensate content of tobacco smoke) of rod-shaped articles as a function of the first and second signals, and generating third signals which denote the actual selected characteristic of the articles. The method further comprises the step of influencing the at least one characteristic of the articles as a function of third signals so as to maintain the at least one characteristic substantially unchanged or to maintain the value of the at least one characteristic within a predetermined range.

It has been ascertained that a predetermined regular relationship exists between the first and second parameters on the one hand, and the at least one characteristic of the articles on the other hand. Therefore, the improved method preferably further comprises the step of storing information (e.g., in the form of functional equations) which denotes the predetermined relationship. The step of generating third signals then includes processing the first and second signals in dependency upon the stored information pertaining to the predetermined regular relationship between the two parameters and the at least one characteristic of the articles. If the articles are made from a plurality of different types or blends of comminuted tobacco, the information storing step comprises storing discrete information (e.g., at least one separate functional equation) for each tobacco type or blend, and the step of generating third signals then comprises processing the first and second signals in dependency upon discrete information pertaining to the type or blend of tobacco in the monitored stream.

The influencing step can further include maintaining the hardness of the articles at a substantially constant value. The hardness of articles can be changed in order to ensure that the at least one characteristic reassumes a value within the predetermined range if such value happens to migrate outside of the acceptable range.

The method can further comprise the step of generating a fourth signal which denotes a reference value of the at least one characteristic of the articles, comparing the third signals with the fourth signal, and generating fifth signals which denote deviations of third signals from the fourth signal. The influencing step then includes ascertaining the at least one characteristic of the articles as a function of the fifth signals.

The determining step can include determining a plurality of different characteristics of rod-shaped articles as a function of the first and second signals, and the step of generating third signals then includes generating discrete third signals each of which denotes one actual characteristic of the articles. Such method preferably further comprises the steps of generating fourth signals each denoting a reference value of one of the plurality of characteristics, comparing the third signals with the corresponding fourth signals, generating fifth signals which denote deviations of third signals from the respective or corresponding fourth signals, processing the fifth signals into sixth signals, and influencing at least one of the plurality of characteristics as a function of the sixth signals. Each sixth signal can constitute a sum of the fifth signals. The influencing step can include maintaining the sum at a substantially constant value. The method can further comprise the step of multiplying with a constant the fifth signals denoting deviations of third signals from the respective fourth signals to thus enhance the influencing of the at least one characteristic or of the respective characteristic or characteristics of the articles.

The method can further comprise the step of maintaining the density of the stream at a substantially constant value, and the influencing step of such method can include maintaining the at least one characteristic or each of the plurality of characteristics at a substantially constant value.

The second parameter can be the hardness of the stream or of the rod-shaped articles (i.e., of portions or sections of the stream). Such method can further comprise the step of converting the first and second signals into additional signals which denote the filling power of tobacco. The step of generating third signals can include generating third signals as a function of the first signals and as a function of the additional signals.

Another feature of the invention resides in the provision of an apparatus for making cigarettes and analogous rod-shaped articles from comminuted tobacco and wrapping material. The apparatus comprises means for gathering comminuted tobacco into a stream and for advancing the stream longitudinally, means for draping the stream into wrapping material, means for subdividing the draped stream into rod-shaped articles, means for monitoring a first parameter which constitutes the density of the stream including means for generating first signals denoting the monitored first parameter, means for ascertaining a second parameter which constitutes a parameter (e.g., filling power) of tobacco or a parameter of the stream including means for generating second signals which denote the ascertained second parameter, and control means having input means connected with the two signal generating means and including means for determining at least one selected characteristic of rod-shaped articles as a function of the first and second signals. The control means further comprises means for generating third signals which denote the actual characteristic of the articles.

The apparatus can further comprise means for displaying the third signals or signals which are derived from third signals. Such displaying means is connected with the means for generating third signals.

The apparatus further comprises means (such as a trimming or equalizing device which is used to remove surplus from the tobacco stream) for influencing at least one parameter of the stream as a function of the third signals (or of signals which are derived form third signals) so as to maintaining the at least one characteristic of the articles within a predetermined range or at a preselected value.

Since it has been determined that a predetermined regular relationship exists between the first and second parameters and the at least one characteristic of the articles, the control means preferably comprises a memory for storage of information denoting such relationship. The means for generating third signals preferably comprises means for generating third signals as a function of stored information, i.e., as a function of first and second signals and also as a function of stored information.

The control means can further comprise means for generating fourth signals or reference signals which denote a selected optimum or desired range or value of characteristics of rod-shaped articles, and means for comparing the third signals with the fourth signals and for generating fifth signals which denote deviations of third signals from fourth signals. The aforementioned influencing means is then designed to influence at least one parameter of the stream as a function of the fifth signals so as to maintain the hardness of rod-shaped articles at least substantially constant, as long as the third signals do not deviate from fourth signals. The at least one characteristic can constitute the hardness of rod-shaped articles, and the control means is operative to change the hardness when the third signals deviate from the fourth signals. In such apparatus, the influencing means is directly or indirectly connected with the means for generating fifth signals.

The control means can include means for generating a plurality of fourth signals or reference signals each of which denotes a range of one of a plurality of selected characteristics of rod-shaped articles, means for comparing the third signals with the fourth signals and for generating a plurality of fifth signals each of which denotes deviations of a third signal from the corresponding fourth (reference) signal, and means for processing the fifth signals into sixth signals which are used to regulate the operation of the influencing means. The processing means can comprise a totalizing circuit which totalizes fifth signals denoting all selected characteristics of rod-shaped articles and generates sixth signals each of which represents a sum of fifth signals denoting deviations of different characteristics of articles from reference values (fourth signals). The influencing means can be designed to maintain the sixth signals at a substantially constant value.

The control means can further comprise means for multiplying one or more fifth signals with a constant to thereby underscore or emphasize the respective selected characteristics of rod-shaped articles.

The influencing means can be designed to operate as a function of first signals (from a density monitoring device) and to maintain one or more selected characteristics of the articles at a substantially constant value.

The apparatus can further comprise means for calculating the filling power of tobacco as a function of the first and second signals and for generating additional signals denoting the ascertained filling power. The means for generating third signals is then designed to generate such third signals as a function of additional signals, i.e., the third signals can be generated as a function of first signals and as a function of additional signals.

The calculating means can be omitted if the apparatus comprises means for directly monitoring the filling power of tobacco.

The means for ascertaining the second parameter of the stream or a parameter of the articles can include means for monitoring the hardness of the stream and/or the hardness of rod-shaped articles.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain presently preferred specific embodiments with reference to the accompanying drawing.

DESCRIPTION OF PREFERRED EMBODIMENTS

Figure 1:
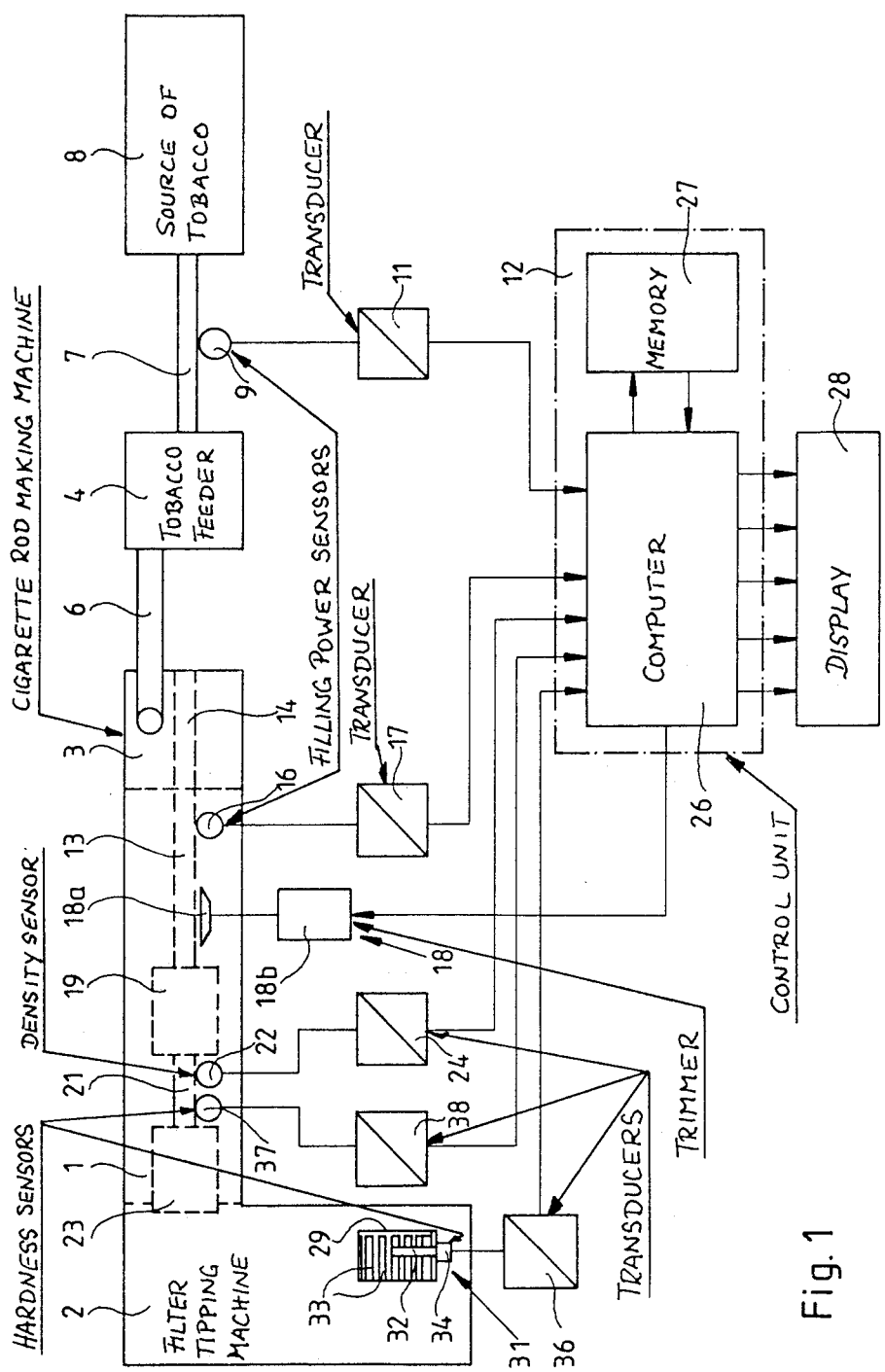
FIG. 1 is a diagrammatic plan view of a cigarette rod making machine including an apparatus which embodies one form of the invention.

Referring first to FIG. 1, there is shown an apparatus which forms part of a cigarette rod making machine 1 and is combined with a filter tipping machine 2. The drawing of FIG. 1 is not to scale. The machine 1 includes a distributor 3 (also called hopper) serving to gather comminuted tobacco (e.g., shreds of tobacco leaf laminae and tobacco ribs) into a continuous stream which is moved longitudinally along a predetermined path defined, at least in part, by a conventional belt conveyor. The cigarette rod making machine 1 can be of the type known as PROTOS, the filter tipping machine 2 can be of the type known as MAX, and the distributor 3 can be of the type known as VE, all produced and distributed by the assignee of the present application. The machine 1 further comprises a magazine 8 for a supply of comminuted tobacco, a tobacco feeder 4 (for example, of the type known as KAB which is produced and distributed by the assignee of the present application), a pneumatic or other suitable conveyor 7 which delivers tobacco from the magazine 8 to the feeder 4, and a pneumatic or other suitable conveyor 6 which transports comminuted tobacco from the feeder 4 into the distributor 3. The conveyor 7 can include or constitute an endless belt conveyor which transports a flow of shredded or otherwise comminuted processed tobacco from the magazine 8 to the feeder 4. The reference character 9 denotes a monitoring device which serves to ascertain the filling power of tobacco and to generate corresponding signals denoting the ascertained filling power. The monitoring device 9 can be of the type described and shown in commonly owned U.S. Pat. No. 4,586,517 granted May 6, 1986 to Wochnowski. The output of the monitoring device 9 is connected with a transducer 11 which transmits appropriate converted signals (denoting the filling power of tobacco on the conveyor 7) to the corresponding input of a computer 26 forming part of a control unit 12.

The distributor 3 includes a stream building unit 14 which converts the incoming comminuted tobacco into a continuous stream, and such stream is advanced along a stream guide 13 (indicated by broken lines) in a direction to the left, as seen in FIG. 1. The guide 13 directs the stream along a path which is adjacent a second monitoring device 16, e.g., a device of the type disclosed in published British patent application No. 2 182 836. A transducer 17 is connected with the output of the monitoring device 16 to transmit appropriate signals (denoting the filling power of tobacco in the stream advancing along the guide 13) to the corresponding input of the computer 26 in the control unit 12. The monitoring device 9 can be used with or in lieu of the monitoring device 16.

The guide 13 further extends along a surplus removing device 18 (hereinafter called trimmer for short) which removes the surplus of tobacco from the stream in the guide and thereby influences at least one parameter of the stream. The illustrated trimmer 18 comprises one or more rotary trimming discs 18a adjacent the guide 13 and a motor 18b which can rotate the disc or discs 18a and can also move with the disc or discs toward or away from the guide 13 so as to cause removal of different quantities of tobacco and to thus influence the stream in different ways. Trimmers which can be used in the machine 1 are disclosed, for example, in commonly owned U.S. Pat. No. 4,564,028 granted Jan. 14, 1986 to Heitmann and in commonly owned U.S. Pat. No. 4,651,755 granted Mar. 24, 1987 to Rudszinat.

The trimmer 18 is followed by a wrapping mechanism 19 (also called format) which drapes the trimmed stream into a web of cigarette paper or other suitable wrapping material to form a wrapped stream 21 (i.e., a cigarette rod) which advances past a density monitoring device 22, e.g., a device known as NSR which is produced and distributed by the assignee of the present application and can include a source of corpuscular radiation at one side of the path for the rod 21 and an ionization chamber at the other side of the rod opposite the radiation source. The output of the monitoring device 22 is connected with a transducer 24 which transmits appropriate signals (denoting the density of successive increments of the filler of the rod 21) to the corresponding input of the computer 26 in the control unit 12. The cigarette rod 21 (draped stream) is subdivided into discrete rod-shaped articles 33 of unit length or multiple unit length in a conventional cutoff 23, and such articles (plain cigarettes of unit length or multiple unit length) are delivered into the filter tipping machine 2 for conversion into filter cigarettes.

The computer 26 of the control unit 12 is connected with a function generator 27 and with a display unit 28 which displays the information transmitted by the corresponding outputs of the computer.

The filter tipping machine 2 comprises a testing conveyor 29 in the form of a rotary drum serving to advance, rod-shaped articles 33 past a hardness monitoring device 31 employing a pivotable lever 32 which is movably mounted in a carrier 34 and comes to rest on successive articles 33 so that its position is indicative of the hardness of tested articles. The monitoring device 31 is connected with a transducer 36 which transmits appropriate signals (denoting the hardness of tested articles 33) to the corresponding input of the computer 26. The extent of deformation of an article 33 under the weight of the lever 32 is proportional to the hardness of such article. Reference may be had to commonly owned copending patent application Ser. No. 261,840 filed Oct. 24, 1988 by Uwe Heitmann.

FIG. 1 merely shows a single drum-shaped conveyor (29) of the filter tipping machine 2. This machine actually comprises a large number of drum-shaped and other conveyors. Reference may be had to commonly owned U.S. Pat. No. 4,177,670 granted Dec. 11, 1979 to Uwe Heitmann et al. which shows a filter tipping machine with a plurality of drum-shaped and other conveyors.

A further hardness monitoring device 37, which can be used in addition to or in lieu of the monitoring device 31, is adjacent the draped tobacco stream 21 immediately downstream of the density monitoring device 22 and transmits signals to a transducer 38 which, in turn, transmits appropriate signals (denoting the hardness of successive increments of the draped stream) to the corresponding input of the computer 26 in the control unit 12. A device which can directly ascertain the hardness of successive increments of a draped tobacco stream is disclosed, for example, in British Pat. No. 1,437,935 or in U.S. Pat. No. 4,615,342 granted Oct. 7, 1986 to Federle et al.

At least one of the monitoring devices 9 and 16 transmits signals which denote the filling power of tobacco in the tobacco stream. Each of the devices 9 and 16 monitors the filling power ahead of the (surplus removing) station for the trimmer 18. It is possible to employ both filling power monitoring devices and to compare the characteristics of signals which are transmitted by the respective transducers 11 and 17 in order to ascertain the accuracy and reliability of the monitoring devices 9 and 16.

The nuclear density monitoring device 22 of the type NSR can be replaced with any other suitable density monitoring device, e.g., a device which operates with infrared light in a manner as disclosed in published British patent application No. 2 179 444. If desired, the measurement of density can be carried out ahead or behind the trimmer 18 upstream of the wrapping mechanism 19, for example, in a manner as disclosed in published British patent application No. 2 182 836.

As already mentioned above, the manufacturers of cigarettes attribute particular importance to adherence of certain selected characteristics of cigarettes to prescribed norms. The most important characteristics are the hardness of cigarettes, their draw resistance (i.e., the resistance a cigarette offers to the flow of smoke), the quantity of certain ingredients (such nicotine, condensate (tar) and carbon monoxide (CO) in tobacco smoke, and the period of combustion (the number of puffs the smoker can make per cigarette).

It has been discovered that a predetermined regular relationship exists between (1) the above-enumerated characteristics of rod-shaped articles (cigarettes 33), (b) a first parameter which is the density of the stream of comminuted tobacco, and (c) a second parameter which is the filling power of tobacco or the hardness of the tobacco stream or the hardness of cigarettes 33. Such predetermined regular relationship can be expressed in the form of functional equations. The following Table lists functional equations for certain selected characteristics of cigarettes 33.

TABLE 1

| | | |
|---|---|---|
| H | $= K_{11} \cdot G - K_{12} \cdot F + K_{13}$ | in mm ET |
| P | $= K_{21} \cdot G + K_{22} \cdot F - K_{23}$ | in mm WS |
| Z | $= K_{31} \cdot G + K_{32} \cdot F - K_{33}$ | in p.p.c. |
| Ni | $= K_{41} \cdot G + K_{42} \cdot F - K_{43}$ | in mg/cig. |
| CO | $= K_{51} \cdot G + K_{52} \cdot F - K_{53}$ | in ml/cig. |
| TK | $= K_{61} \cdot G + K_{62} \cdot F + K_{63}$ | in mg/cig. |

In the above Table, H denotes the hardness of cigarettes 33 in mm penetration depth (ET) as measured in accordance with the so-called Borgwald technique; G is the weight of cigarettes, P is the draw resistance in mm water column (WS); Z is the period of combustion of a cigarette in puffs per cigarette (p.p.c.); Ni is the nicotine content in mg per cigarette; CO is the carbon monoxide content in ml per cigarette; and TK is the condensate (tar) content in mg per cigarette. The character F denotes the filling power of tobacco.

In principle, the above functional equations are valid for all tobacco types and all tobacco blends. However, the coefficients or constants $K_{in}$ (wherein $1 \leq i \leq 6$ and $1 \leq n \leq 3$) will differ from tobacco blend to tobacco blend and from tobacco type to tobacco type and are ascertained empirically for each tobacco blend or type. Specific coefficients or constants K for a particular tobacco blend are furnished in the following Table.

TABLE 2

| | | | |
|---|---|---|---|
| H | $= 0.0027$ G | $- 0.0706$ F $+ 6.665$ | in mm ET |
| P | $= 0.152$ G | $+ 4.58$ F $- 137.6$ | in mm WS |
| Z | $= 0.0178$ G | $+ 0.0856$ F $- 6.23$ | in p.p.c. |
| Ni | $= 0.001$ G | $+ 0.0104$ F $- 0.27$ | in mg/cig. |
| CO | $= 0.016$ G | $+ 0.408$ F $- 6.8$ | in ml/cig. |
| TK | $= 0.0039$ G | $+ 0.285$ F $+ 8.46$ | in mg/cig. |

The coefficients for use in the aforediscussed functional equations must be determined only once for each tobacco blend or for each tobacco type. Such determination can be readily carried out by resorting to well known laboratory techniques which need not be described here.

Figure 2:
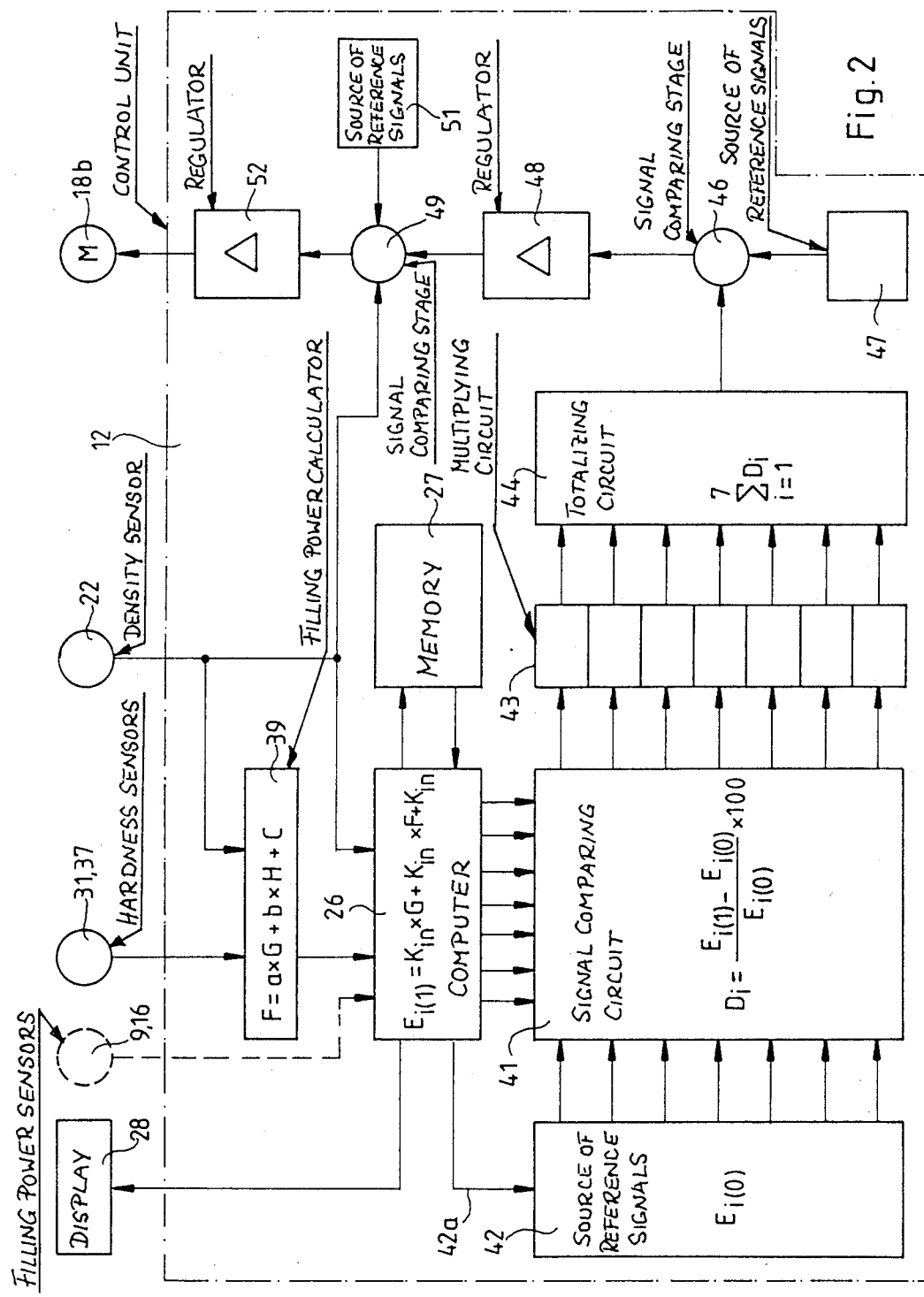
FIG. 2 is a block diagram of the control unit in the apparatus of FIG. 1.

FIG. 2 is a schematic block diagram of elements in a presently preferred embodiment of the control unit 12. This control unit can be used to select, in advance, certain characteristics of cigarettes 33 on the basis of the aforediscussed predetermined regular relationship between two parameters of tobacco, tobacco stream or cigarettes on the one hand, and one or more selected characteristics of cigarettes on the other hand. In other words, the control unit 12 renders it possible to optimize the making of the tobacco stream for the purpose of ensuring that one or more selected characteristics of rod-shaped articles 33 will assume predetermined optimum values or will closely approach such optimum values.

The function generator 27 of the control unit 12 is a memory for the aforementioned functional equations denoting the predetermined regular relationship between selected characteristics of cigarettes 33 and the two parameters (of the stream, tobacco and/or cigarettes). The control unit 12 further comprises the aforementioned computer 26 which constitutes a means for generating (on the basis of first signals, e.g., from the density monitoring device 22, and on the basis of second signals, e.g., from the filling power monitoring device 9 or 16) third signals denoting the actual values of the characteristics of cigarettes 33. As mentioned above, the transducers 11, 17, 24, 36 and 38 (which, in turn, are connected to the respective monitoring devices 9, 16, 22, 31 and 37) are connected to the corresponding inputs of the computer 26. The transducers for the monitoring device 22 and the monitoring device 31 and/or 37 are further connected to a filling power calculator 39 the output of which is connected with an input of the computer 26. The calculator 39 ascertains the filling power of tobacco on the basis of the equation $F = a \cdot G + b \cdot H + c$. Thus, the calculator 39 establishes a predetermined relationship between the hardness H and the weight G (i.e., density in order to ascertain the filling power F. Density is proportional to the weight G of cigarettes.

The connection between the filling power monitoring device 9 and/or 16 and the computer 26 is optional; therefore, such connection is indicated in FIG. 2 by broken lines. If the monitoring device 9 and/or 16 transmits signals denoting the filling power of tobacco directly to the computer 26, the filling power calculator 39 can be dispensed with.

The computer 26 processes (first) signals from the monitoring device 22 and (second) signals from the calculator 39 on the basis of functional equations in the function generator (memory) 27 to generate third signals which denote the actual values of selected characteristics of the cigarettes 33. Such signals can be displayed at 28 so that one can continuously monitor the expected or anticipated characteristics of the cigarettes.

The motor 18b of the trimmer 18 can be adjusted and operated as a function of computed values. This renders it possible to set up the cigarette rod making machine 1 in such a way that at least one selected characteristic of cigarettes 33 assumes and adheres to a constant or practically constant value. By way of example, the trimmer 18 can influence the making of cigarettes 33 in such a way that the nicotine content of cigarettes will remain at least substantially constant. The value of each other selected characteristic of cigarettes 33 is controlled by the regular relationship as expressed by the functional equations in Table 1.

A procedure which has been found to be particularly satisfactory as regards all of the selected characteristics of cigarettes 33 is as follows: The control circuit 12 further comprises a source 42 of reference values for all selected characteristics of the cigarettes. The trimmer 18 removes the surplus at a rate which is a function of density signals (first signals) and hardness signals or filling power signals (second signals) in such a way that the hardness of cigarettes remains constant. As already explained above, the hardness of cigarettes is a characteristic which is particularly important to the smokers.

The hardness of cigarettes remains constant as long as the values of other selected characteristics of cigarettes remain within the respective predetermined ranges of values. However, if one of the characteristics is changed to such an extent that its value is no longer within the prescribed range (for example, because the filling power of a particular blend of tobacco which has replaced the previously processed blend departs considerably from the filling power of the previously processed blend), i.e., that one or more characteristics of the cigarettes are no longer acceptable, the control circuit 12 changes the reference value of hardness of cigarettes (and hence the mode of regulating the hardness of cigarettes) on the basis of functional equations in the memory 27 to an extent which is necessary to ensure that the value or values of one or more selected characteristics of cigarettes return into the corresponding range or ranges of acceptable values (i.e., of tolerances which are acceptable to the manufacturer and/or to the smoker). Thus, such adjustment via control circuit 12 alters the hardness of cigarettes as soon as the filling power of tobacco which is being converted into a stream changes; however, the values of all selected characteristics of the cigarettes remain within the predetermined ranges of acceptable values.

In accordance with another presently preferred embodiment, the apparatus is operated in such a way that the values of all selected characteristics of cigarettes are continuously optimized during operation of the rod making machine 1. To this end, seven outputs of the computer 26 are connected to the corresponding inputs of a signal comparing circuit 41 wherein (third) signals denoting the actual characteristics of cigarettes are compared with (fourth) signals from the source 42 of reference signals and which generates (fifth) signals $D_i$ denoting deviations of the third signals (from 26) from the respective fourth signals (from 42). The source 42 of reference signals contains the desired values for all of the selected characteristics of cigarettes 33, namely of all characteristics which are related to each other in a manner as expressed by the functional equations in Table 1. The reference values can be transmitted to the source 42 by hand (e.g., by resorting to a keyboard). However, it is also possible to store in the source 42 signals which are transmitted by the computer 26 and have been found to be an optimum set of reference values for comparison with third (actual value) signals which are transmitted from the computer 26 to the signal comparing circuit 41. The transmission of such set of optimum signals from the computer 26 to the source 42 of reference signals can take place by way of conductor means 42a.

The fifth signals $D_i$ (wherein $1 \leq i \leq 7$) which are generated by the signal comparing circuit 41 are indicative of deviations of third signals (transmitted by the computer 26) from the corresponding fourth signals (transmitted by the source 42 of reference signals), and such deviations can be calculated in percent. The outputs of the signal comparing circuit 41 are connected with the corresponding inputs of a signal multiplying circuit 43 wherein the fifth signals are multiplied by a predetermined factor prior to being transmitted to a signal totalizing circuit 44 which forms a sixth signal corresponding to the sum of fifth signals transmitted by the signal comparing circuit 41 via signal multiplying circuit 43. The (sixth) signal at the output of the totalizing circuit 44 is transmitted to a stage 46 wherein such signal is compared with a reference signal from a source 47 of reference sum signals. The signal from the source 47 is indicative of the desired sum of $D_i$, and such sum is normally zero. The stage 46 transmits a control signal which is indicative of deviation of signal transmitted by the totalizing circuit 44 from the signal which is transmitted by the source 47 of reference sum signals, and the control signal from the stage 46 passes through a regulator 48 prior to being transmitted to a further signal comparing stage 49. The latter further receives signals from the density monitoring device 22 and from a source 51 of reference signals denoting the desired density of the stream.

The elements 22, 49, 51 and 18 of the circuit which is shown in FIG. 2 form part of a density regulating arrangement wherein the trimmer 18 is the output element which directly influences the stream of comminuted tobacco. Such density regulating arrangement can be influenced by signals from the regulator 48, i.e., by signals denoting deviations of the signal transmitted by the totalizing circuit 44 from the signal transmitted by the source 47 of reference sum signals. The reference character 52 denotes a regulator which is installed between the output of the signal comparing stage 49 and the motor 18b of the trimmer 18. The aforementioned regulator 48 between the signal comparing stages 46 and 49 can constitute a PI regulator.

Under normal circumstances, the density (i.e., weight) regulating arrangement including the signal comparing stage 49 regulates the operation of the trimmer 18 in such a way that the latter influences the stream of comminuted tobacco in a sense to maintain the density of the stream at a constant value. This ensures that the value of each selected characteristics of cigarettes 33 remains within an acceptable range as long as the filing power F of tobacco in the stream remains unchanged. On the other hand, it is very difficult and often impossible to invariably ensure that the filling power of tobacco which is being gathered in the unit 14 to form a continuous stream remains unchanged. The reason is that the filling power F can be influenced by a host of variables including the moisture content of tobacco, the temperature of tobacco, changes of conditions in the means for expelling moisture from tobacco, changes in the distribution of longer and shorter tobacco shreds in the stream, and certain specific characteristics of comminuted tobacco which is being transported from the magazine 8 toward and into the stream building unit 14. The just enumerated variables can fluctuate by as much as 10 percent.

In heretofore known cigarette rod making machines, minor departures of filling power of tobacco from the selected or desired value are simply disregarded even though such minor fluctuations of filling power exert a readily detectable influence upon selected characteristics of rod-shaped smokers' products, such as plain cigarettes. In such conventional machines, consideration is given only to changes in weight which are attributable to changes of filling power, namely all weight or density of the stream is maintained at a constant value. On the other hand, changes of filling power of tobacco cause fluctuations of all or nearly all such characteristics of cigarettes which influence the quality of cigarettes. The effect upon the quality of cigarettes is especially unsatisfactory if the regulation merely involves maintaining the weight of cigarettes at a constant value. The above drawbacks of conventional methods and machines are eliminated in accordance with the present invention in the following way.

The computer 26 calculates the values of selected characteristics $E_i$ of cigarettes on the basis of the general formula $E_{i(1)} = K_{in} \cdot G + K_{in} \cdot F + K_{in}$ (wherein $1 \leq i \leq 7$ and $1 \leq n \leq 3$). In this formula, $E_i$ denotes the characteristic hardness H, draw resistance P, combustion period p.p.c., condensate (tar) content TK, nicotine content Ni and carbon monoxide content CO. The symbol $E_{i(1)}$ denotes the actual values of the just enumerated characteristics. The coefficients $K_{in}$ are different for each tobacco blend or each tobacco type and are stored in the memory (function generator) 27.

As long as the filling power F of tobacco remains constant, the actual values $E_{i(1)}$ of selected characteristics of cigarettes also remain constant because the density regulating arrangement 18, 22, 49, 51, 52 maintains the density (and hence the weight G) of the tobacco stream at a constant value. Under such circumstances, the actual values of all selected characteristics of cigarettes are located on the zero line of the bar graph of FIG. 3. This zero line denotes the correspondence or identity of actual values with reference signals $E_{i(0)}$ which are transmitted by the source 42 of reference signals, i.e., the actual values do not deviate from the respective reference values. In the beam graph of FIG. 3, D denotes (in percent) deviations of actual values from the corresponding reference values, and such deviations are determined by the signal comparing circuit 41 in accordance with the equation $$D_i = \frac{E_{i(1)} - E_{i(0)}}{E_{i(0)}} \cdot 100.$$

Figure 3:
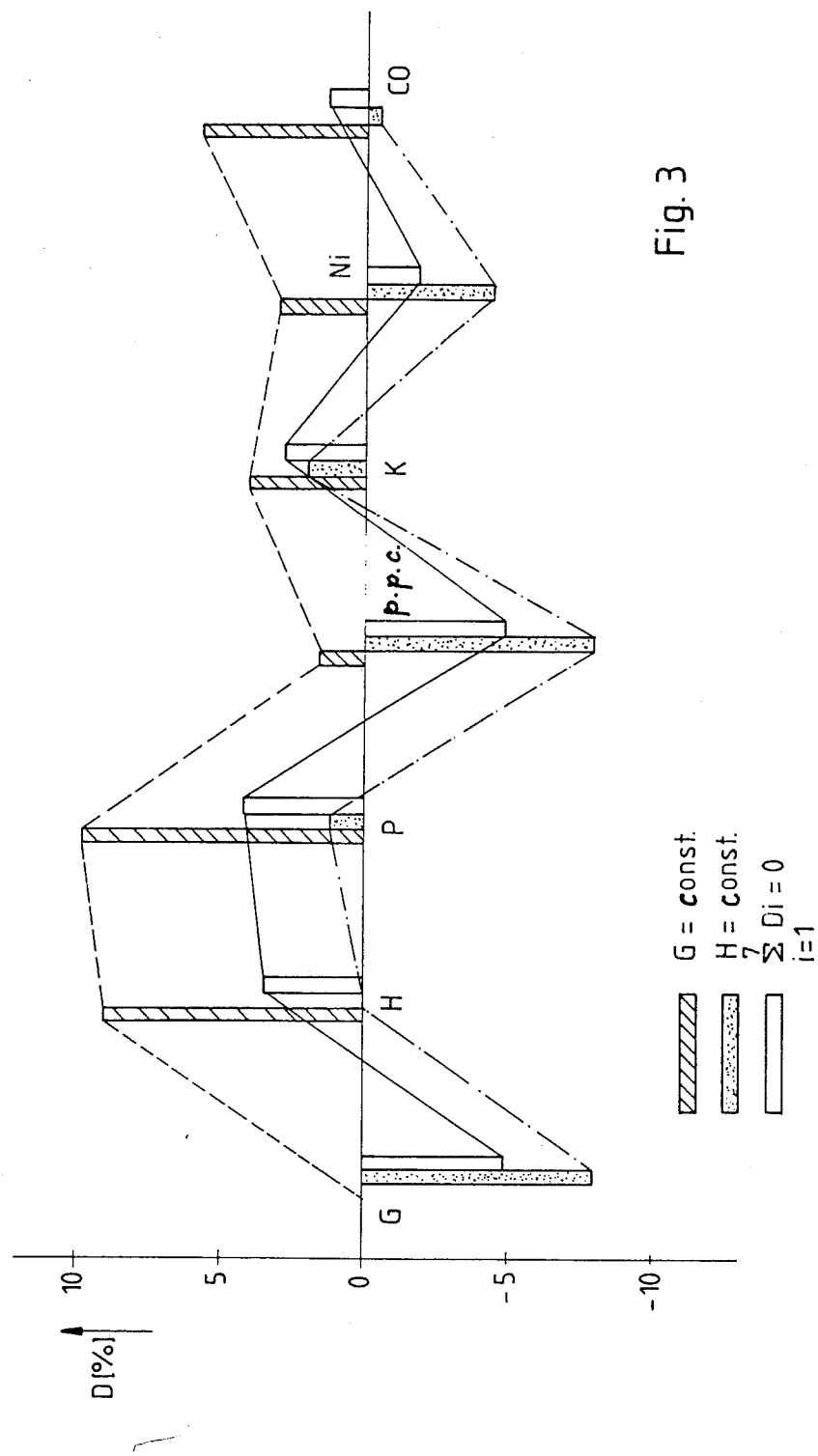
FIG. 3 is a bar graph showing the values of various characteristics of cigarettes which are produced in accordance with conventional methods and in accordance with the method of the present invention.

If the filling power F rises by 10 percent while the machine 1 is in the process of making cigarettes 33, all other characteristics of cigarettes change to a different extent in dependency upon the aforediscussed predetermined regular relationships as expressed by the functional equations in Table 1. If one were to maintain only the density (i.e., the weight G) at a constant value in a manner as is customary in heretofore known machines, this would lead in part to considerable departures of actual characteristics of cigarettes from their desirable or optimum characteristics. Such departures are indicated in FIG. 3 by hatched beams which, for the sake of emphasis, are connected to each other by broken lines. The broken lines do not denote any stages of operation or adjustment of the machine 1. The graph of FIG. 3 shows that the density regulating arrangement 18, 22, 49, 51, 52 maintains the density (and hence the weight G) at a constant value as indicated by the zero line. On the other hand, the actual values of certain other characteristics of cigarettes depart from the respective reference values by up to nearly ten percent, such reference values being denoted by the zero line.

If the filling power of tobacco rises by 10 percent and the control unit 12 is designed to maintain the value of hardness H constant (on the zero line of the bar graph of FIG. 3), i.e., not to maintain the value of density and weight G at a constant value, the actual value of hardness remains unchanged (i.e., on the zero line) but the actual values of other characteristics of cigarettes deviate from the respective reference values to a different extent. These deviations are indicated in FIG. 3 by stippled beams which are connected to each other by phantom lines. As shown, the actual values of certain characteristics can depart from the respective reference values by as much as 8 percent.

It will be noted that a regulation to maintain the density or weight G at a constant value (while the filling power F changes) is not entirely satisfactory, the same as a regulation to maintain the hardness H at a constant value. This will be readily appreciated by looking at FIG. 3 which shows that, under such circumstances, the values of other characteristics of cigarettes will fluctuate within a rather wide range. In fact, fluctuations of the values of certain characteristics can be so pronounced that they are totally unacceptable. This problem is overcome by the provision of the aforediscussed totalizing circuit 44 which transmits a signal denoting the sum of all signals $D_i$ (deviations of signals transmitted to 41 by 26 from signals transmitted to 41 by 42). The resulting sum signal is compared (in the stage 46) with the reference sum signal from the source 47, and the stage 46 transmits a control signal which denotes the difference between the actual and reference sum signals. This control signal is superimposed upon the signal which is generated by the density regulating arrangement 18, 22, 49, 51, 52. Such interference into the operation of the density regulating arrangement results in an entirely different influencing of the stream by the trimmer 18, namely the density of the stream is influenced in such a way that all selected characteristics of cigarettes 33 assume optimum values, namely optimum values in view of the filling power of comminuted tobacco in the stream. This is or can be accomplished by appropriate selection of the reference signal in the source 47. The value of the selected reference signal at the output of the source 47 is zero; however, it is possible to select another value without departing from the spirit of the invention.

In the graph of FIG. 3, the unstippled and unhatched beams denote those departures of selected characteristics of cigarettes 33 from optimum characteristics (reference values represented by the zero line) which develop when the operation of the density control arrangement 18, 22, 49, 51, 52 is influenced by signals from the stage 46. It will be noted that deviations of actual values of the selected characteristics G, H, P, p.p.c., K, Ni and CO are much less pronounced than if the weight G or the hardness H were maintained at a constant value in a manner as is customary in conventional cigarette rod making and like machines. For the sake of emphasis, the unstippled and unhatched beams in the graph of FIG. 3 are connected to each other by solid lines. The rise of filling power (plus 10 percent) is the same as in the aforedescribed examples when the weight G or the hardness H remains constant. The value of the reference signal which is transmitted by the source 47 is assumed to be zero. The sum of all deviations of actual values $D_i$ from the reference value is also zero. It will be readily noted that, on the whole, departures of values of selected characteristics of cigarettes from optimum values are less pronounced than those which are indicated by hatched or stippled bars. In other words, the sum of all selected characteristics of cigarettes is much more satisfactory than in the event of regulation of the weight G or hardness H in a manner to maintain the weight or hardness constant.

The multiplying circuit 43 of FIG. 2 is assumed to multiply each signal from the calculator 41 by the factor "1". This ensures that the original underscoring of all selected characteristics of cigarettes, as determined by the relationships which are expressed by the functional equations of Table 1, remains unchanged, the same as the influence of signals from 41 upon the sum signal which is generated by the circuit 44. If one or more signals from the signal comparing circuit 41 to the totalizing circuit 44 are multiplied by a factor other than "1", the corresponding signals are emphasized in a different way (depending upon the selected multiplication factor), i.e., the influence of such signals upon the sum signal which is generated by the circuit 44 is different from the influence of other signals which are multiplied by the factor "1". In this manner, the operator of the rod making machine 1 can influence, within certain limits, the deviations $D_i$ of signals transmitted by 26 to 41 from signals transmitted by 42 to 41. Deviations of the value of any selected characteristic of cigarettes 33 in percent from the respective reference value can be selected practically at will; however, this will or can cause (as a rule) rather pronounced deviations of actual values of other characteristics from the respective reference values in view of the aforediscussed predetermined regular relationship which exists between various selected characteristics of cigarettes and is defined by the functional equations of Table 1. An analogous influencing of deviations (in percent) of actual values of certain selected characteristics of cigarettes from the corresponding reference values can be achieved by appropriate selection of the reference signal which is transmitted by the source 47.

As shown in FIG. 2, signals denoting the filling power F can be transmitted directly from the monitoring device 9 and/or 16 to the corresponding input of the computer 26. The reason for the provision of filling power calculator 39 is that direct measurements of filling power F at 9 and/or 16 might not be as reliable as those with the calculator 39 in dependency upon the ascertained weight G and hardness H. At the present time, monitoring of hardness with available monitoring devices is considered to be more reliable than a direct determination of filling power of tobacco. Irrespective of whether one relies on the monitoring of hardness or on monitoring of filling power, it is desirable to take into consideration the influence of moisture content of tobacco as well as the influence of temperature of tobacco particles.

Signals which the calculator 39 receives from the monitoring device 22 and from the monitoring device 31 and/or 37 are processed in accordance with the aforediscussed equation for the calculation of the filling power F, and the resulting signals are transmitted to the computer 26. This not only exhibits the advantage that the calculator 39 can process the more reliable signals denoting the hardness H but also that the filling power signal is independent of the density signal as long as a change of density is not caused by a change of filling power. This also contributes to greater reliability of actual value (third) signals which the computer 26 transmits to the circuit 41.

The circuit 41 generates deviation signals $D_i$ of seven different characteristics of cigarettes 33 even though the memory 27 stores only six functional equations (note the Table 1). The reason is that the computer 26 also transmits to the circuit 41 signals which denote actual weight G of cigarettes 33. Such signals are generated by the transducer 24 on the basis of signals which are transmitted thereto by the density monitoring device 22. Signals which denote the weight G are compared with corresponding reference signals from the source 41, and the signals $D_i$ denoting deviations of actual values of G from the corresponding reference values are transmitted to the totalizing circuit 44 via multiplying circuit 43.

The circuit 41 can embody an averaging circuit which averages the integrals of several successive deviation signal $D_i$ and transmits the thus averaged signals to the circuit 43 for multiplication and transmission to the totalizing circuit 44. This results in a desirable smoothing of short-lasting deviations of actual value signals from the respective reference values with attendant steadying of operation of the control circuit 12 and of the influencing means (trimmer) 18.

FIG. 2 illustrates the control circuit 12 in the form of a block diagram for the purpose of facilitating an understanding of the mode of its operation. In actual practice, a modern high-speed cigarette rod making machine will normally employ a signal processing unit in the form of an integrated circuit or a computer which does not or need not embody all discrete elements of the illustrated control circuit 12 but performs all functions of the illustrated elements with the same results.

An important advantage of the improved method and apparatus is that it is now possible to determine in advance, the actual value of one or more important characteristics of cigarettes by the simple expedient of monitoring the density of the tobacco stream (such as with the monitoring device 22) and monitoring another parameter of the stream or a parameter of tobacco (such as with the monitoring device 31 and/or 37). These important characteristics include the draw resistance, the period of combustion (puffs per cigarette), the nicotine content of tobacco smoke, the condensate (tar) content of tobacco smoke, the hardness of cigarettes and the carbon monoxide content of tobacco smoke.

Another important advantage of the improved method and apparatus is that the values which are determined in advance can be displayed at 28. A mere inspection of displayed information is of considerable help to attendants in evaluating the operation of the machine which embodies the improved apparatus and in assessing the quality of the products.

As mentioned above, an important aspect of the invention is based on the recognition that there exist predetermined regular relationships between various important characteristics of cigarettes and that such relationships can be accurately expressed in terms of functional equations which can be stored in a memory and addressed by the computer 26 for determination of (third) signals which are to be transmitted to the signal comparing circuit 41. The memory 27 stores a set of functional equations for each type and each blend of tobacco.

A further important aspect of the invention resides in the recognition that the production of cigarettes can be optimized and that one can ensure a highly desirable homogeneousness of various characteristics of cigarettes by the provision of the source 42 which furnishes reference values for the values of all selected characteristics of cigarettes and by regulating the removal of surplus by the trimmer 18 in dependency on the measured values of density and the other parameter (such as filling power F) in such a way that the hardness of cigarettes remains constant, as long as the actual values of selected characteristics of the cigarettes remain within the ranges which are denoted by signals from the source 42. If the actual values of selected characteristics migrate to such an extent that they are outside of the respective ranges, the control unit 12 simply ensures that the reference value of hardness of cigarettes is altered in a sense to ensure that actual values of the selected characteristics are changed until they are again within the prescribed ranges. Continuous on-line measurements of density and of the second parameter of the stream or of a parameter of tobacco invariably ensure that the control unit 12 can continuously regulate the operation of the trimmer 18 in a sense to ensure that the values of selected characteristics of cigarettes will not depart from desired or optimum values to an extent which would exceed acceptable tolerances.

The source 42 can store signals which are indicative of the exact optimum or desired values of various selected characteristics of the cigarettes, and the control unit 12 then operates in such a way that the operation of the trimmer 18 (i.e., of the means for influencing a parameter of the stream) is regulated with a view to ensure that selected values of the characteristics of cigarettes are adhered to. This constitutes one of the presently preferred embodiments of the improved method. The display unit 28 can be used to display information which denotes the values of actual value (third) signals transmitted by the computer 26 and/or deviations of such signals from the respective reference (fourth) signals which are transmitted by the source 42.

An advantage of the group of elements including the signal comparing stage 46, the totalizing circuit 44 and the source 47 of reference sum signals is that deviation signals which are transmitted by the stage 46 are a highly reliable indicator of the quality of cigarettes as represented by the values of their selected characteristics. Therefore, a signal denoting the sum of signals $D_i$ at the output of the totalizing circuit 44 is suited to serve as an actual value signal which can be used to regulate the operation of the machine 1 by controlling the operation of the trimmer 18. The regulation is preferably such that the sum signal at the output of the circuit 44 assumes and retains a preselected value.

The improved method and apparatus render it possible to regulate the operation of the trimmer 18 in a standard manner (provided that the circumstances are satisfactory for such mode of regulation, especially because the filling power of tobacco remains unchanged) by the simple expedient of causing the arrangement including the elements 18, 22, 49, 51 and 52 to regulate the operation of the trimmer 18 for the purpose of ensuring that the density of the stream remains constant. This ensures that, under the just outlined circumstances, the important characteristics of cigarettes remain unchanged. The operation of the trimmer 18 is influenced in accordance with the invention when this becomes necessary in view of certain changes of circumstances, particularly a change of the filling power of tobacco, because this would result in drastic and undesirable changes of the values of selected characteristics of cigarettes, especially if the filing power F were to change while the density would remain constant. At such time, the operation of the arrangement including the parts 18, 22, 49, 51 and 52 is controlled by signals from the stage 46, i.e., by signals denoting the sum of deviations $D_i$.

The second parameter which is monitored for the purpose of generating second signals is the filling power F of tobacco or the hardness of the draped stream and/or of cigarettes 33 (i.e., of sections of the draped stream).

The provision of the calculator 39 is based on the recognition that a certain relationship exists between the density of the tobacco stream, the hardness of the tobacco stream and the filling power F of tobacco. This relationship can be expressed by the aforementioned formula $F = a \cdot G + b \cdot H = c$. As explained above, such mode of ascertaining the filling power F of tobacco is believed to be more reliable and more accurate than direct monitoring of filling power by the device 9 and/or 16. As also mentioned above, the calculator 39 exhibits the additional advantage that a signal denoting tHe filling power F does not change when the monitored change of hardness is based solely on a change of density, i.e., if the change of hardness is not brought about by a change of filling power.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A method of making cigarettes and analogous rod-shaped articles from comminuted tobacco and wrapping material, comprising the steps of gathering comminuted tobacco into a stream and advancing the stream longitudinally; draping the stream into wrapping material; subdividing the draped stream into rod-shaped articles; monitoring a first parameter which constitutes the density of the stream; ascertaining a second parameter which constitutes a parameter of tobacco or of the stream; generating first and second signals which respectively denote the first and second parameters; determining a plurality of different characteristics of rod-shaped articles as a function of said first and second signals; generating discrete third signals each denoting one actual characteristic of rod-shaped articles; generating fourth signals each denoting a reference value of one of said plurality of characteristics; comparing said third signals with the corresponding fourth signals; generating fifth signals denoting deviations of third signals from the corresponding fourth signals; processing said fifth signals into sixth signals, including forming a sum of said fifth signals; and influencing at least one of said plurality of characteristics as a function of said sixth signals.

2. The method of claim 1, further comprising the step of influencing at least one of said characteristics of the articles as a function of said third signals so as to maintain the value of said at least one characteristic at least substantially unchanged.

3. The method of claim 1, wherein a predetermined relationship exists between said parameters and at least one of said characteristics, and further comprising the step of storing information denoting said relationship, said step of generating third signals including processing said first and second signals in dependency upon said information.

4. The method of claim 3 of making articles from a plurality of different blends or types of comminuted tobacco, wherein said information storing step comprises storing discrete information for each blend or type, said step of generating third signals including processing said first and second signals in dependency upon discrete information pertaining to the type or blend of tobacco in the monitored stream.

5. The method of claim 1, wherein said influencing step includes maintaining said sum at a substantially constant value.

6. Apparatus for making cigarettes and analogous rod-shaped articles from comminuted tobacco and wrapping material, comprising means for gathering comminuted tobacco into a stream and for advancing the stream longitudinally; means for draping the stream into wrapping material; means for subdividing the draped stream into rod-shaped articles; means for monitoring a first parameter which constitutes the density of the stream, including means for generating first signals denoting the monitored density; means for ascertaining a second parameter which constitutes a parameter of tobacco or of the stream, including means for generating second signals denoting the second parameter; control means having input means connected with said signal generating means and including means for determining at least one selected characteristic of rod-shaped articles—other than said first and second parameters—as a function of said first and second signals, means for generating third signals denoting the actual characteristic of the articles, means for generating fourth signals denoting a selected range of characteristics of rod-shaped articles, and means for comparing said third signals with said fourth signals and for generating fifth signals denoting deviations of said third signals from said fourth signals; and means for influencing at least one parameter of the stream as a function of said fifth signals so as to maintain the hardness of the articles substantially equal to a predetermined constant as long as said third signals do not deviate from said fourth signals, said control means including means for modifying said predetermined constant when said third signals deviate from said fourth signals so as to effect a return of said third signals to within said selected range.

7. The apparatus of claim 6, further comprising means for displaying said third signals, said displaying means being connected with said means for generating third signals.

8. The apparatus of claim 6, further comprising means for influencing at least one parameter of the stream as a function of said third signals so as to maintain said at least one characteristic of the articles within a predetermined range.

9. The apparatus of claim 6, wherein a predetermined relationship exists between said parameters and said at least one characteristic, said control means comprising a memory for storage of information denoting said relationship, said means for generating third signals including means for generating third signals as a function of said information.

10. The apparatus of claim 6, wherein said at least one characteristic is the density of articles.

11. The apparatus of claim 7, wherein said influencing means is connected with said comparing means.

12. The apparatus of claim 6, wherein said control means further comprises means for processing said fifth signals into sixth signals, and further comprising means for influencing at least one parameter of the stream as a function of said sixth signals.

13. The apparatus of claim 12, wherein said control means further comprises means for multiplying said fifth signals with a constant to underscore a selected characteristic of the articles.

14. The apparatus of claim 6, wherein said gathering means includes means for forming a stream which contains a surplus of comminuted tobacco, and further comprising means for influencing at least one parameter of the stream as a function of said third signals including means for removing the surplus from the stream.

15. The apparatus of claim 6, wherein said means for ascertaining a second parameter includes means for monitoring the hardness of the stream or the hardness of rod-shaped articles.

16. A method of making cigarettes and analogous rod-shaped articles from comminuted tobacco and wrapping material, comprising the steps of gathering comminuted tobacco into a stream and advancing the stream longitudinally; draping the stream into wrapping material; subdividing the draped stream into rod-shaped articles; monitoring a first parameter which constitutes the density of the stream; ascertaining a second parameter which constitutes a parameter of tobacco or of the stream; generating first and second signals which respectively denote the first and second parameters; determining at least the hardness of rod-shaped articles as a function of said first and second signals; generating third signals denoting the actual hardness of rod-shaped articles; and influencing the hardness of articles as a function of said third signals so as to maintain the hardness of articles at a substantially constant value.

17. The method of claim 16, further comprising the step of changing the hardness of articles when the at least one characteristic is outside of said range.

18. A method of making cigarettes and analogous rod-shaped articles from comminuted tobacco and wrapping material, comprising the steps of gathering comminuted tobacco into a stream and advancing the stream longitudinally; draping the stream into wrapping material; subdividing the draped stream into rod-shaped articles; monitoring a first parameter which constitutes the density of the stream; ascertaining a second parameter which constitutes the hardness of the stream or of rod-shaped articles; generating first and second signals which respectively denote the first and second parameters; determining at least one selected characteristic of rod-shaped articles as a function of said first and second signals; generating third signals denoting the actual selected characteristic of rod-shaped articles; and converting said first and second signals into additional signals denoting the filling power of tobacco, said step of generating third signals including generating third signals as a function of said first and said additional signals.

19. The method of claim 18, further comprising the steps of generating a fourth signal denoting a reference value of said at least one characteristic, comparing said third signals with said fourth signal, generating fifth signals denoting deviations of third signals from said fourth signal, and influencing said at least one characteristic as a function of said fifth signals.

20. The method of claim 19, further comprising the step of multiplying said fifth signals with a constant to enhance the influencing of said at least one characteristic.

21. The method of claim 19, further comprising the step of maintaining the density of the stream at a substantially constant value, said influencing step including maintaining said at least one characteristic at a substantially constant value.

22. Apparatus for making cigarettes and analogous rod-shaped articles from comminuted tobacco and wrapping material, comprising means for gathering comminuted tobacco into a stream and for advancing the stream longitudinally; means for draping the stream into wrapping material; means for subdividing the draped stream into rod-shaped articles; means for monitoring a first parameter which constitutes the density of the stream, including means for generating first signals denoting the monitored density; means for ascertaining a second parameter which constitutes a parameter of tobacco or of the stream, including means for generating second signals denoting the second parameter; control means having input means connected with said signal generating means and including means for determining at least one selected characteristic of rod-shaped articles as a function of said first and second signals, means for generating third signals denoting the actual characteristic of the articles, means for generating a plurality of fourth signals each denoting a range of one of a plurality of selected characteristics of the articles, means for comparing said third signals with said fourth signals and for generating a plurality of fifth signals each denoting deviations of a third signal from the corresponding fourth signal, and means for processing said fifth signals into sixth signals including means for totalizing said fifth signals; and means for influencing at least one parameter of the stream as a function of said sixth signals.

23. The apparatus of claim 22, wherein said influencing means includes means for maintaining said sixth signals at a substantially constant value.

24. Apparatus for making cigarettes and analogous rod-shaped articles from comminuted tobacco and wrapping material, comprising means for gathering comminuted tobacco into a stream and for advancing the stream longitudinally; means for draping the stream into wrapping material; means for subdividing the draped stream into rod-shaped articles; means for monitoring a first parameter which constitutes the density of the stream, including means for generating first signals denoting the monitored density; means for ascertaining a second parameter which constitutes a parameter of tobacco or of the stream, including means for generating second signals denoting the second parameter; control means having input means connected with said signal generating means and including means for determining at least one selected characteristic of rod-shaped articles as a function of said first and second signals, and means for generating third signals denoting the actual characteristic of the articles; and means for calculating the filling power of tobacco as a function of said first and second signals and for generating additional signals denoting the ascertained filling power, said means for generating third signals including means for generating third signals as a function of said first signals and said additional signals.

25. Apparatus for making cigarettes and analogous rod-shaped articles from comminuted tobacco and wrapping material, comprising means for gathering comminuted tobacco into a stream and for advancing the stream longitudinally; means for draping the stream into wrapping material; means for subdividing the draped stream into rod-shaped articles; means for monitoring a first parameter which constitutes the density of the stream, including means for generating first signals denoting the monitored density; means for ascertaining a second parameter which constitutes a parameter of tobacco or of the stream, including means for generating second signals denoting the second parameter; control means having input means connected with said signal generating means and including means for determining at least one selected characteristic of rod-shaped articles as a function of said first and second signals, means for generating third signals denoting the actual characteristic of the articles, means for generating fourth signals denoting a selected range of characteristics of rod-shaped articles, means for comparing said third signals with said fourth signals and for generating fifth signals denoting deviations of said third signals from said fourth signals, and means for processing said fifth signals into sixth signals; means for regulating the density of the stream as a function of said first signals; and means for influencing the density of the stream as a function of said sixth signals for maintaining said at least one characteristic of the articles within said selected range.

26. Apparatus for making cigarettes and analogous rod-shaped articles from comminuted tobacco and wrapping material, comprising means for gathering comminuted tobacco into a stream and for advancing the stream longitudinally; means for draping the stream into wrapping material; means for subdividing the draped stream into rod-shaped articles; means for monitoring a first parameter which constitutes the density of the stream, including means for generating first signals denoting the monitored density; means for monitoring the filling power of tobacco, including means for generating second signals denoting the filling power; control means having input means connected with said signal generating means and including means for determining at least one selected characteristic of rod-shaped articles as a function of said first and second signals, means for generating third signals denoting the actual characteristic of the articles, means for generating fourth signals denoting a selected range of characteristics of rod-shaped articles, and means for comparing said third signals with said fourth signals and for generating fifth signals denoting deviations of said third signals from said fourth signals; and means for influencing at least one parameter of the stream as a function of said fifth signals so as to maintain the hardness of the articles substantially constant as long as said third signals do not deviate from said fourth signals.

* * * * *